(12) United States Patent
Vecchio et al.

(10) Patent No.: US 11,398,022 B2
(45) Date of Patent: Jul. 26, 2022

(54) APPARATUS FOR THE ANALYSIS OF SAMPLES TAKEN BY BIOPSY

(71) Applicant: IMS GIOTTO S.P.A., Sasso Marconi (IT)

(72) Inventors: Sara Vecchio, Casalecchio di Reno (IT); Paolo Vignoli, San Giovanni in Persiceto (IT)

(73) Assignee: IMS GIOTTO S.P.A., Sasso Marconi (IT)

( * ) Notice: Subject to any disclaimer, the term of this patent is extended or adjusted under 35 U.S.C. 154(b) by 982 days.

(21) Appl. No.: 16/134,292

(22) Filed: Sep. 18, 2018

(65) Prior Publication Data

US 2019/0130563 A1 May 2, 2019

(30) Foreign Application Priority Data

Oct. 27, 2017 (IT) .................. 102017000122588

(51) Int. Cl.
*G06T 7/00* (2017.01)
*A61B 10/02* (2006.01)
*A61B 17/34* (2006.01)
*G01N 33/483* (2006.01)
*A61B 6/00* (2006.01)
*A61B 90/17* (2016.01)
(Continued)

(52) U.S. Cl.
CPC .......... *G06T 7/0012* (2013.01); *A61B 6/0414* (2013.01); *A61B 6/502* (2013.01); *A61B 6/545* (2013.01); *A61B 6/547* (2013.01); *A61B 10/02* (2013.01); *A61B 10/0233* (2013.01); *A61B 17/3403* (2013.01); *A61B 90/17* (2016.02); *G01N 33/4833* (2013.01); *A61B 2010/009* (2013.01); *A61B 2090/376* (2016.02); *G06T 2207/30004* (2013.01)

(58) Field of Classification Search
CPC ...... G06T 7/0012; A61B 90/17; A61B 6/0414
See application file for complete search history.

(56) References Cited

U.S. PATENT DOCUMENTS

2008/0081984 A1 4/2008 Lafferty
2014/0241500 A1 8/2014 Yasuda et al.
(Continued)

FOREIGN PATENT DOCUMENTS

CN 102481146 A 5/2012
CN 105934200 A 9/2016
(Continued)

OTHER PUBLICATIONS

Italian Search Report dated Jun. 29, 2018 from counterpart Italian App No. IT 201700122588.
(Continued)

*Primary Examiner* — Hugh Maupin
(74) *Attorney, Agent, or Firm* — Shuttleworth & Ingersoll, PLC; Timothy J. Klima

(57) ABSTRACT

An apparatus and a method for analysing samples taken by biopsy, which make it possible to perform the analysis of these samples whilst the patient is still positioned in the position for taking samples, in such a way as to make the overall procedure for taking and analysing the samples faster, reducing the inconvenience for the patient and the risk of a new examination, and also reducing in the majority of cases exposure of the patient to X-rays.

17 Claims, 9 Drawing Sheets

(51) Int. Cl.
    *A61B 6/04*     (2006.01)
    *A61B 10/00*     (2006.01)
    *A61B 90/00*     (2016.01)

(56) References Cited

U.S. PATENT DOCUMENTS

| | | |
|---|---|---|
| 2016/0113599 A1 | 4/2016 | Albanese et al. |
| 2016/0310215 A1* | 10/2016 | Palma .................... A61B 90/39 |
| 2017/0020473 A1 | 1/2017 | Klausz et al. |
| 2017/0082557 A1 | 3/2017 | Iordache et al. |
| 2018/0168523 A1 | 6/2018 | Vancamberg et al. |

FOREIGN PATENT DOCUMENTS

| | | |
|---|---|---|
| CN | 106361359 A | 2/2017 |
| CN | 106901761 A | 6/2017 |
| JP | 2015085056 A | 5/2015 |
| WO | WO2018085719 A1 | 5/2018 |

OTHER PUBLICATIONS

Chinese Office Action dated Jan. 17, 2022 from counterpart Chinese Patent Application No. 201811247953.2.

\* cited by examiner

APPARATUS FOR THE ANALYSIS OF SAMPLES TAKEN BY BIOPSY

This application claims priority to Italian Patent Application 102017000122588 filed Oct. 27, 2017, the entirety of which is incorporated by reference herein.

BACKGROUND OF THE INVENTION

The invention relates to an apparatus and a method for analysing samples taken by biopsy, which make it possible to perform the analysis of these samples whilst the patient is still positioned in the position for taking samples, in such a way as to make the overall procedure for taking and analysing the samples faster, reducing the inconvenience for the patient and the risk of a new examination, and also reducing in the majority of cases exposure of the patient to X-rays.

SUMMARY OF THE INVENTION

Currently, in order to the perform the bioptic taking of lesions identified as suspicious in the body of the patient, one of the possibilities when the lesion is radiopaque is the use of an apparatus for the X-ray analysis of at least a part of the body of the patient, by which a research of the suspicious lesion in this part of that body of the patient is performed. When the suspicious lesion has been found in the X-ray image, its position is determined by means of further X-ray images (pointing) and a step of taking one or more samples by means of a biopsy is performed, in order to sample a part or all of the suspicious lesion, in order to subsequently analyze by cytological or histological examination.

During the step for taking samples by means of biopsy or at least before the demission of the patient it is good practice to carry out a check by X-ray of the samples already taken to confirm that the sample contains the same anatomic element considered suspicious in the image of the patient and that the procedure for determining the position of the lesion and for its sampling has therefore been successfully completed. In the case of unforeseen events, this checking allows an immediate repetition of the pointing, without having to arrange a new appointment for the patient and it reduces the risk of diagnostic errors from the biological analysis of the sample due to incorrect sampling. The X-ray checking may be performed using a further apparatus specifically for this purpose or by means of the same type of apparatus with which the suspicious lesion has been identified, but always separate with respect to the apparatus with which the pointing is performed.

The aim of this invention is to provide an apparatus and/or a method for the analysis of samples taken by biopsy, which allows the analyses to be performed with the same apparatus with which the pointing and sampling is performed when the patient is still in the position for taking the samples, and also without requiring the patient to adopt an uncomfortable position during the analysing step or having to withdraw the needle for taking the samples from the patient.

In addition to the benefit for the patient, the use of the same system for both the procedures (the one of pointing with subsequent taking and checking of the samples) is a guarantee of the same quality of result and thus of consistency between the results of the two analyses (identifying the target for taking and checking the presence of the target in the sample taken).

Another aim of this invention is to provide an apparatus and/or a method for the analysis of samples taken by biopsy which allows these analyses to be performed when the patient is still is in the position for taking the samples and limiting (for example, minimizing or avoiding completely), during the step of analysing the samples performed by means of the apparatus, an unnecessary exposure of the body of the patient to X-rays.

These aims are achieved by an apparatus having features as disclosed herein or by a method having features as disclosed herein.

The features of an apparatus according to this invention and of a method according to this invention will become clearer from the detailed description below relating to a possible embodiment of the apparatus and to a possible embodiment of the method, given by way of non-limiting examples of the concepts claimed.

BRIEF DESCRIPTION OF THE DRAWINGS

The following detailed description refers to the accompanying drawings, in which.

DESCRIPTION OF THE PREFERRED EMBODIMENTS

Figure 1:
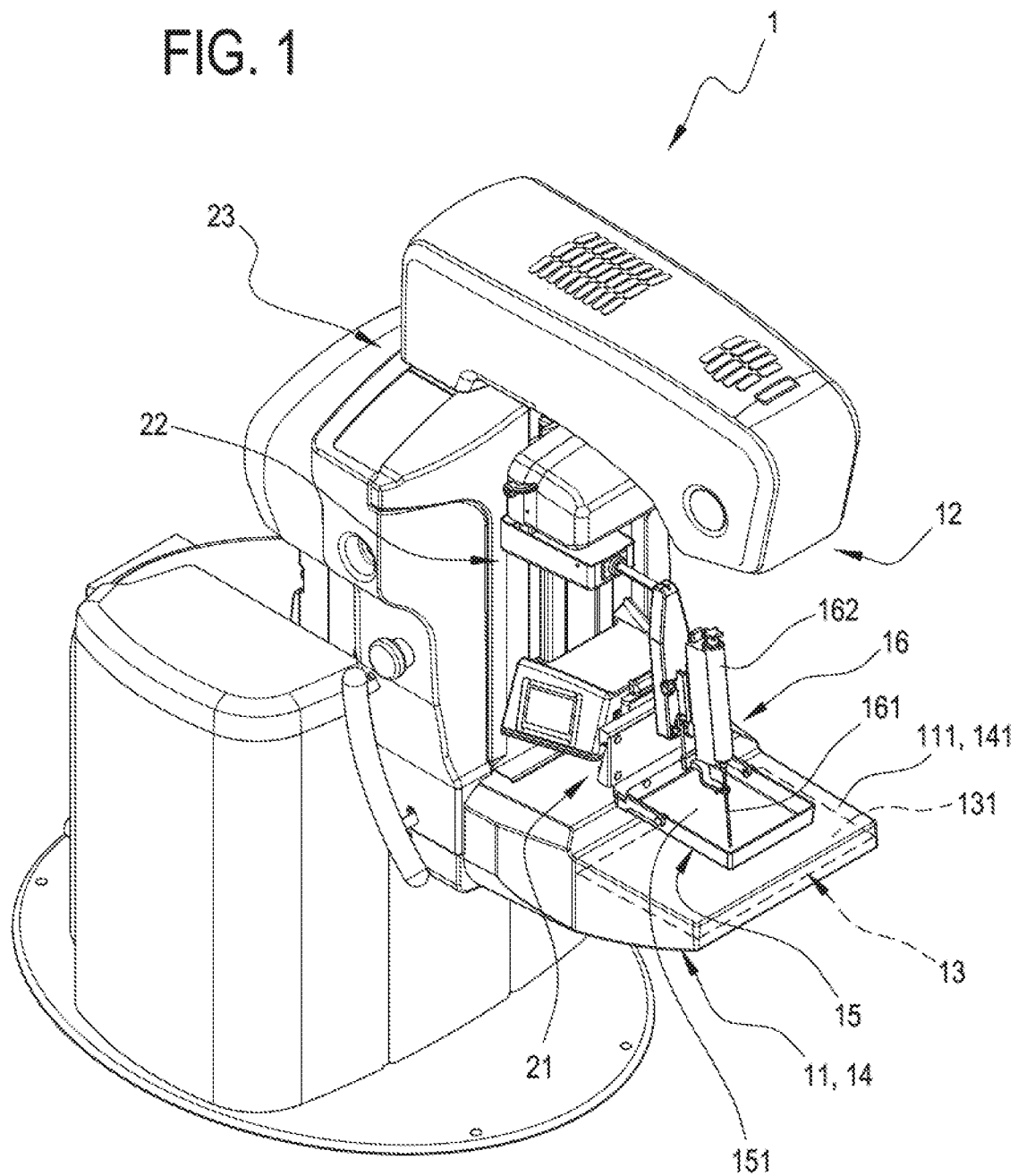
FIG. 1 is a perspective view of a possible embodiment according to the invention.

In the accompanying drawings the numeral 1 denotes a possible embodiment of an apparatus according to the invention. The apparatus 1 is configured for the analysis of samples. These samples are to be considered as taken from a part of the body of a person.

The apparatus comprises a support 11 for these samples. The support 11 defines a supporting surface 111. The supporting surface 111 is designed for positioning the samples on the supporting surface 111.

The apparatus 1 comprises a system 12 for generating a field of X-rays. The generating system 12 is configured for generating the field of X-rays.

The generating system 12 is configured so that the field can adopt a plurality of different operating conditions.

The apparatus comprises an X-ray detector 13. The detector 13 defines a detection surface 131. The detector 13 is configured to detect the image of X-rays incident on the detection surface 131. The apparatus 1 is configured in such a way that, when the field adopts any of the operating conditions, the X-rays of the field strike the detection surface 131 after striking the supporting surface 111. In that way, also by means of the configuration of the support 11, the apparatus 1 is configured in such a way that, when the field adopts any of the operating conditions and any object any is positioned inside the field and on the supporting surface 111, the apparatus 1 can perform, by means of the generating system 12 and the detection system 13, an acquiring of at least one X-ray image of the any object.

Since the any object can be considered as a corresponding to the above-mentioned samples, this means that the apparatus 1 allows the acquiring of at least one X-ray image of the samples, whilst they are positioned on the supporting surface 111 and inside the field.

The generating system 12 is configured so that the operating conditions differ from each other for the orientation and/or the position of the field of X-rays with respect to the detection surface 131 and/or for at least the value of a dimension of the field of X-rays.

In an example use of the apparatus 1, the field of X-rays can be considered as a cone of X-rays.

Figure 8:
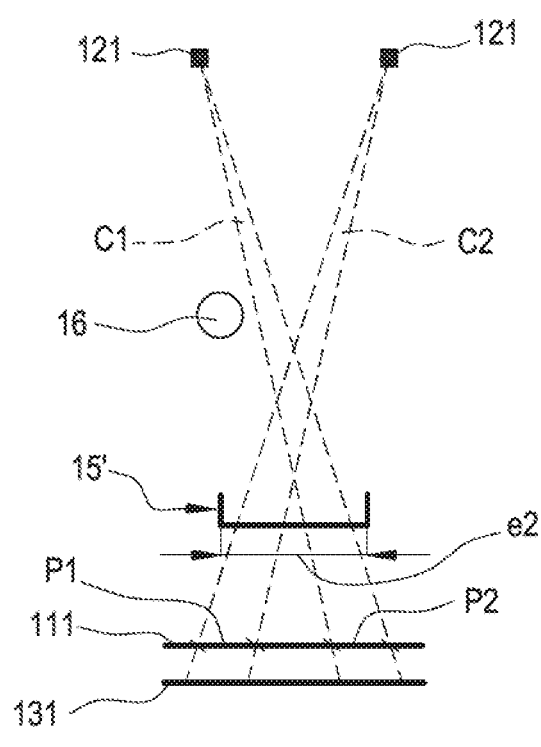
FIG. 8 schematically illustrates a first operating condition and a second operating condition which can be adopted by a field of X-rays generated using the apparatus of FIGS. 1-2.

C1 in FIG. 8 denotes the field when it adopts a first example operating condition and C2 denotes the field when it adopts a second example operating condition. C3 in FIG. 9 denotes the field when it adopts a third example operating condition.

Figure 9:
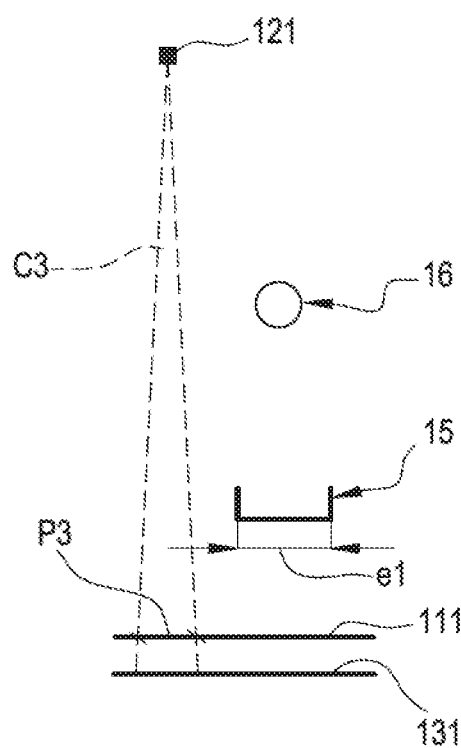
FIG. 9 schematically illustrates a third operating condition which can be adopted by the field.

In FIGS. 8 and 9, a profile of the supporting surface 111 and the detection surface 131 are shown according to a front view of the apparatus 1. It should be noted that, even though all the Figures from 3 to 9 are front views of the apparatus 1, FIGS. 8 and 9 only show some components of the apparatus 1. Moreover, the components of the apparatus 1 are shown schematically in FIGS. 8 and 9, to explain possible differences in mutual positions of these components.

Figure 4:
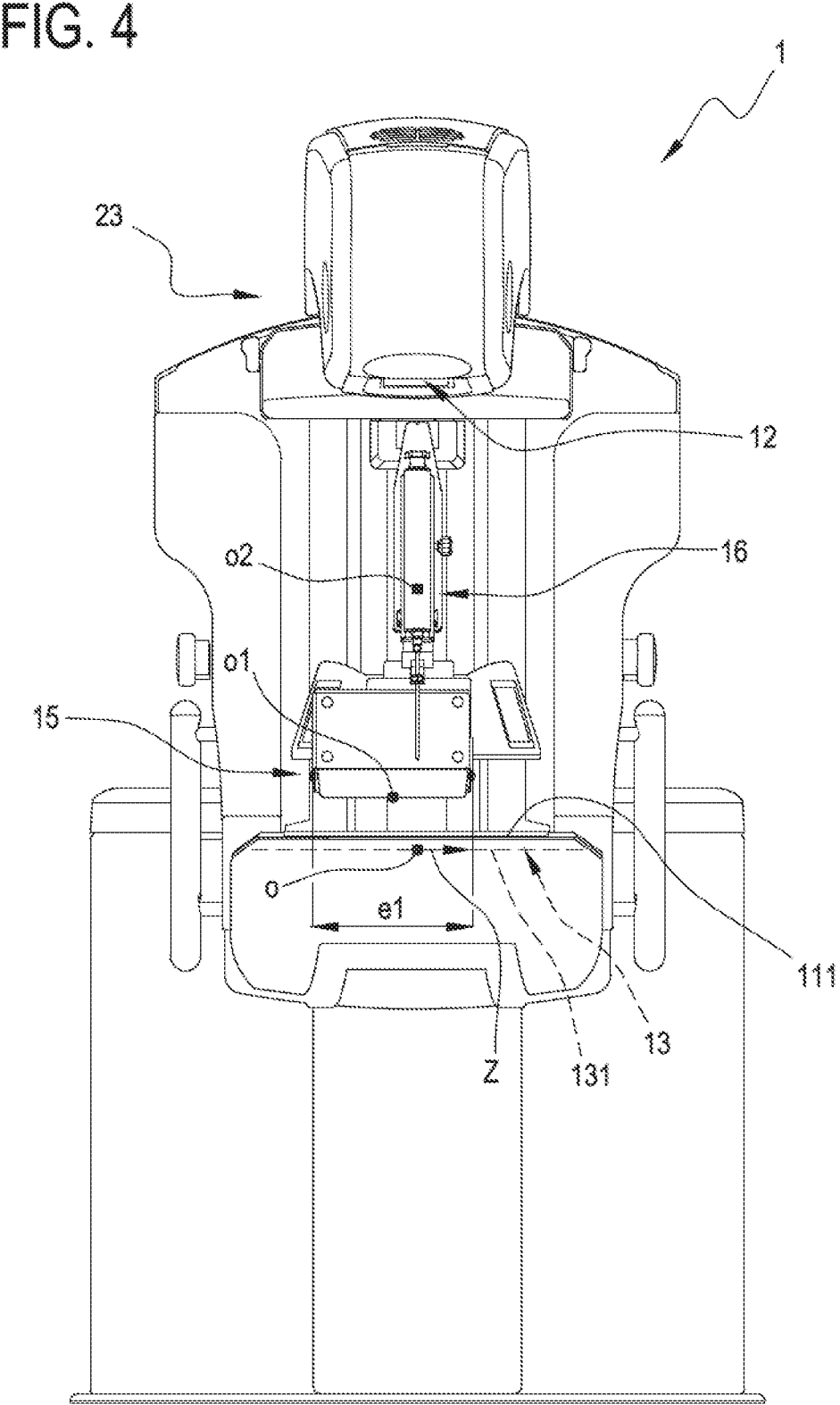

It is possible to define a reference system integral with the detection surface 131. The reference system is defined by a set of three axes of which a first axis Z and a second axis Y are positioned and/or lying on the detection surface 131. The first axis Z and second axis Y are shown, by means of the respective versors, in FIG. 10. The versor of the first axis Z is also shown in FIG. 4. The point of origin of the reference system integral with the detection surface 131 is labelled "o" in FIG. 10 and in FIG. 4.

The third axis of the reference system, which is not shown in the drawings, is at right angles to the first axis Z and second axis Y.

To generate the field of X-rays, the generating system 12 comprises an X-ray source 121. The source 121 is schematically represented as a dot in FIGS. 8 and 9.

The source 121 can generate X-rays designed to give rise to the field of X-rays. To ensure that the field of X-rays can adopt one or other of the plurality of operating conditions, and therefore to ensure that it can adopt these operating conditions, the generating system 12 comprises a collimator and a movement system.

The movement system is labelled 23 in FIGS. 1-7.

A position of the source 121 with reference to the above-mentioned reference system integral with the detection surface 131 may be considered as a "position of the source 121 with respect to the detection surface 131".

The generation system 12 is configured so that the movement system 23 can cause a movement of the source 121 in such a way that the source 121 can adopt a plurality of different positions relative to the detection surface 131.

In FIG. 8, the source 121, where is represented at the vertex of the field labelled C1, is in a first position relative to the detection surface 131. In FIG. 8, the source 121, where is represented at the vertex of the field labelled C2, is in a second position relative to the detection surface 131. In FIG. 9, even if the field of X-rays adopts a third operating condition labelled C3, and the operating condition is different from the operating condition C1 of FIG. 8, the source 121 is in the above-mentioned first position.

This movement of the source 121 may be performed, for example, along a curved trajectory.

The generation system 12 is configured so that the collimator can adopt a plurality of operating configurations associated with a plurality of collimation modes respectively. Each of the respective plurality of collimation modes is associated with a respective one of the operating configurations of the collimator and derives from the fact that the collimator adopts the respective operating configuration. The generation system 12 is configured so that the collimator can follow the movement of the source 121. The generating system 12 is configured so that, when the collimator adopts any one of these operating configurations, and when the source 121 adopts any one of these positions of the source 121 relative to the detection surface 131, the collimator is adjusted to allow the passage of the X-rays emitted by the source 121 in accordance with the collimation mode with which the operating configuration adopted by the collimator is associated, in such a way as to define the operating condition adopted by the field of X-rays. As a result, each of the operating conditions of the field is defined by a respective combination of one of the positions of the source 121 and of one of the configurations of the collimator. The variation of the operating configuration of the collimator, if the field is considered as a cone X-rays, can determine a variation at least of the angle of the cone and/or a variation at least of the orientation of the cone relative to the detection surface 131. The variation of the position of the source 121 relative to the detection surface 131 can determine a variation at least of the orientation of the cone relative to the detection surface 131.

The difference between the first operating condition of the field, labelled C1 in FIG. 8, and the third operating condition of the field, labelled C3 in FIG. 9, is that, even though the source 121 is, for both the first and third operating conditions, in the same position relative to the detection surface 131, the operating configuration of the collimator is different in the first operating condition relative to the third operating condition.

The apparatus 1 comprises a support 14. The support 14 defines a supporting surface 141 for resting the above-mentioned part of the body of a person on the supporting surface 141. The support 11 can be also defined as a "first support 11" and the support 14 can be also defined as a "second support 14". Therefore, the supporting surface 111 can be also defined a "first supporting surface 111" and the supporting surface 141 can be also defined a "second supporting surface 141".

The apparatus 1 is configured in such a way that, when the field adopts any of the operating conditions, the X-rays of the field strike the detection surface 131 after striking the supporting surface 141. In that way, also by means of the configuration of the support 14, the apparatus 1 is configured in such a way that, when the field adopts any of the operating conditions and the part of the body is positioned inside the field and on the supporting surface 141, the apparatus 1 can perform, by means of the generating system 12 and the detection system 13, an acquiring of at least one X-ray image of the part of the body.

The acquiring of at least one X-ray image of the part of the body may be aimed at identifying a possible area of the part of the body in which a lesion or suspicious mass could be positioned.

In the embodiment illustrated, the detector 13 is integrated in the support 14.

In the embodiment illustrated, the detection surface 131 may be in a fixed position relative to the supporting surface 141.

In the embodiment illustrated, the support 11 coincides with the support 14, in such a way that the supporting surface 111 coincides with the supporting surface 141. In the light of the above, in this case, the first support 11 coincides with the second support 14 and the first supporting surface 111 coincides with the second supporting surface 141.

The supporting surface 111 might, however, not coincide with or be completely separate from the supporting surface 141. The support 11 might not coincide with or be completely separate from the support 14.

The support 11 could be removable from the remaining part of the apparatus 1.

The apparatus 1 comprises a biopsy probe 16 in order to take the above-mentioned samples from the above-mentioned part of the body of a person.

The probe 16 may comprise a sampling element 161 to perform the sampling. The probe 16 may comprise a support 162 to support the sampling element 161. The sampling element 161 may be a needle.

The sampling may be a biopsy. In this case, the samples are to be considered as taken by biopsy.

The apparatus 1 is configured so that the probe 16 can be subjected to a movement through the field and/or relative to the detection surface 131. The movement of the probe 16 is used to ensure that the position which the probe 16 adopts whilst taking the samples is as correct as possible in order to increase the probability that the samples belong to the above-mentioned lesion or suspicious mass.

The step during which the probe 16 moves to increase the probability that the samples subsequently taken belong to this lesion or suspicious mass may be defined as "pointing". The pointing is basically guided by the X-ray images of the part of the body which have been previously acquired for identifying the above-mentioned possible zone of the part of the body in which this lesion or suspicions mass could be positioned.

The above-mentioned acquiring of at least one X-ray image of the samples whilst they are positioned in this field and on the support 11, is aimed at check that the samples actually belong to this lesion or suspicious mass.

A position of the probe 16 relative to the detection surface 131 may be considered, which is to be considered as a position of the probe 16 relative to the above-mentioned reference system integral with the detection surface 131.

This movement of the probe 16 is designed to cause the variation of the position of the probe 16.

The movement of the probe 16 could comprise at least a translational component. An example of this translational component is indicated by the double arrows T2 in FIG. 3. The translational component could be along the above-mentioned first axis Z.

The position of the probe 16 comprises at least the height at which a reference point of the probe 16 is positioned along and/or relative to the first axis Z. The reference point of the probe 16 is labelled o2 in FIG. 4. The height may be defined as the height of the probe 16 along the first axis Z.

The translational component of the movement of the probe 16 is designed to cause the variation of the height of the probe 16.

The probe 16 is schematically represented in FIGS. 8 and 9 as a circle. The height of the probe 16 in FIG. 8 adopts a first value. In FIG. 9, the height of the probe 16 adopts a second value different from the first value.

Figure 2:
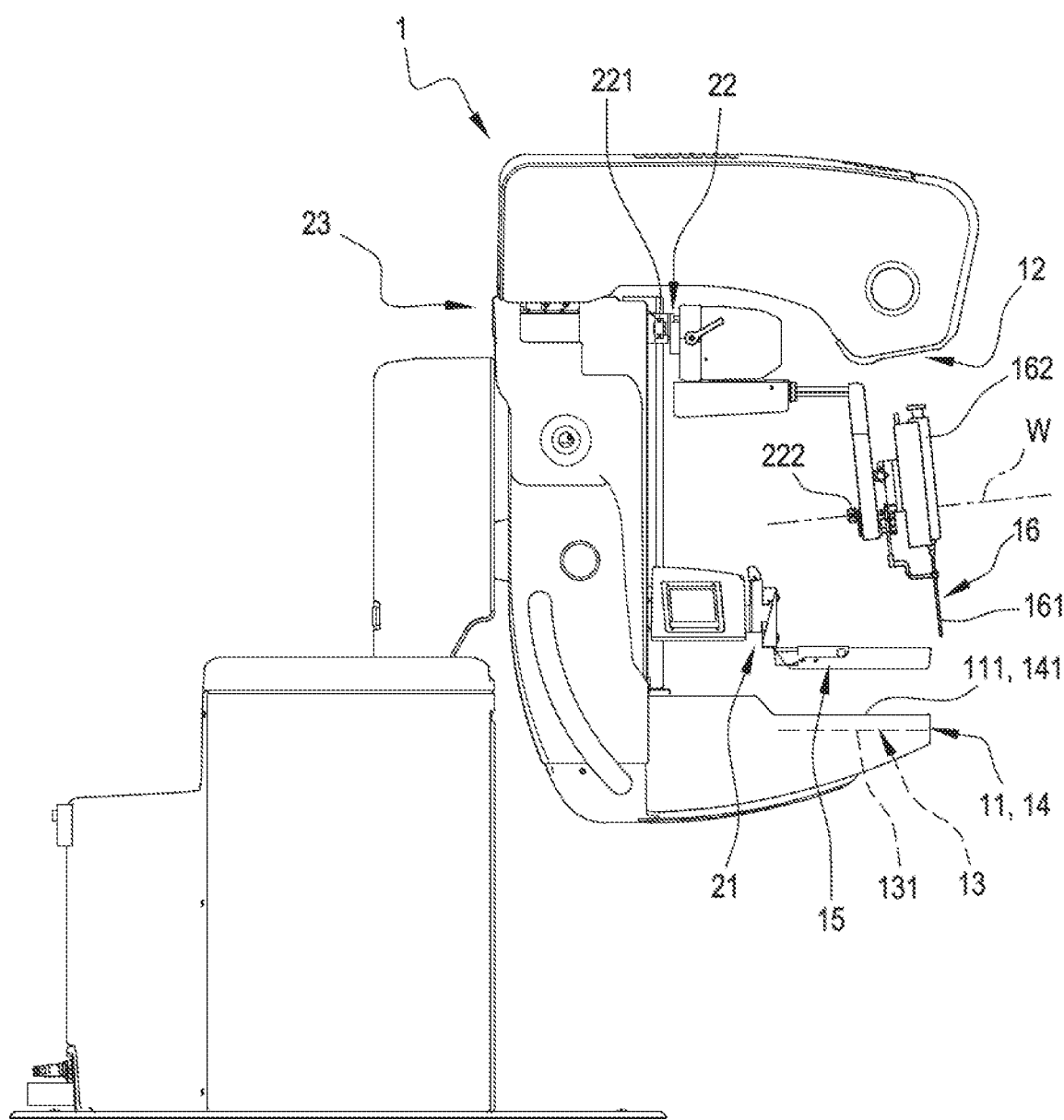
FIG. 2 is a side view of the apparatus of FIG. 1.
Figure 3:
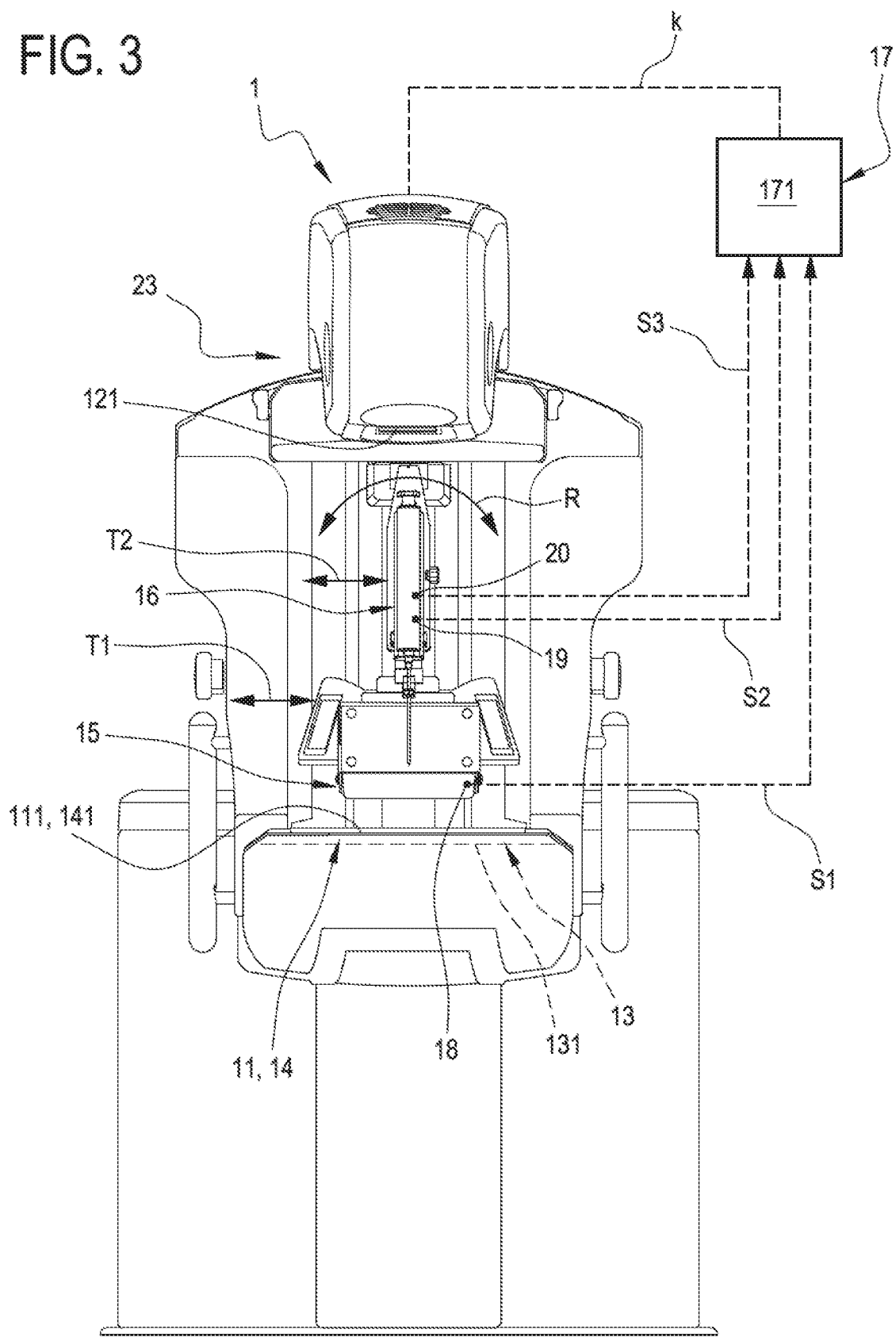
FIGS. 3 to 5 show front views of the apparatus of FIGS. 1-2, in a situation in which a stabilizing element of the apparatus is of a first type and adopts, respectively, three different positions.

The movement of the probe 16 could comprises at least a rotational component. The rotational component is a rotation on itself of the probe 16. The rotation occurs about an axis of rotation which remains integral with the above-mentioned translational component of the movement of the probe 16. The projection of this rotation on the plane of FIG. 3 is indicated by the double arrows R of FIG. 3. The axis of rotation is labelled W in FIG. 2. The reference point o2 of the probe 16, indicated in FIG. 4, is conventionally positioned, in the drawings, in such a way that the axis of rotation W passes through the reference point o2 of the probe 16.

This position of the probe 16 could be also considered as comprising at least the angular orientation of the probe 16 around the above-mentioned axis of rotation W and relative to the above-mentioned reference system which is integral with the detection surface 131.

The rotational component of the movement of the probe 16 is designed to cause the variation of the orientation of the probe 16.

So as to cause the movement of the probe 16, the apparatus comprises a system for movement of the probe 16. The movement system of the probe 16 is labelled 22 in FIGS. 1 and 2. As can be seen in FIG. 2, the movement system 22 of the probe 16 comprises a first part 221 which is designed to cause the above-mentioned translational component of movement of the probe 16. As can be seen in FIG. 2, the movement system 22 of the probe 16 comprises a second part 222 which is designed to cause the above-mentioned rotational component of the movement of the probe 16.

The movement of the probe 16 might also comprise a translational component along the second axis Y lying on the detection surface 131 and/or a translational component along an axis at right angles to the first axis Z and the second axis Y.

The apparatus 1 comprises a stabilizing element 15. The stabilizing element 15 extends along a stabilizing surface 151. The apparatus 1 is configured so that the stabilizing element 15 can stabilize the positioning of the above-mentioned part of the body on the supporting surface 141, for taking the samples.

Figure 5:
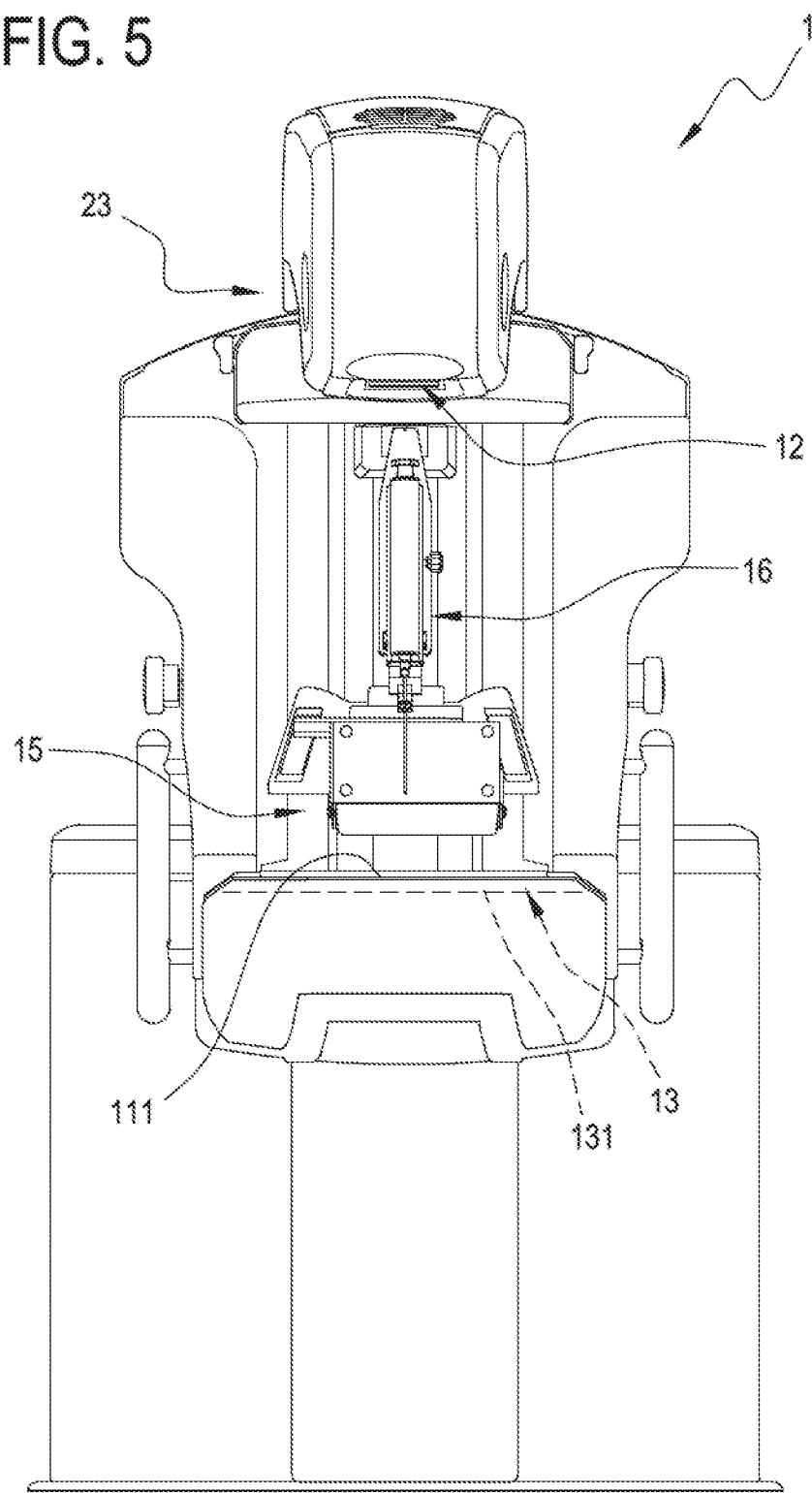
Figure 6:
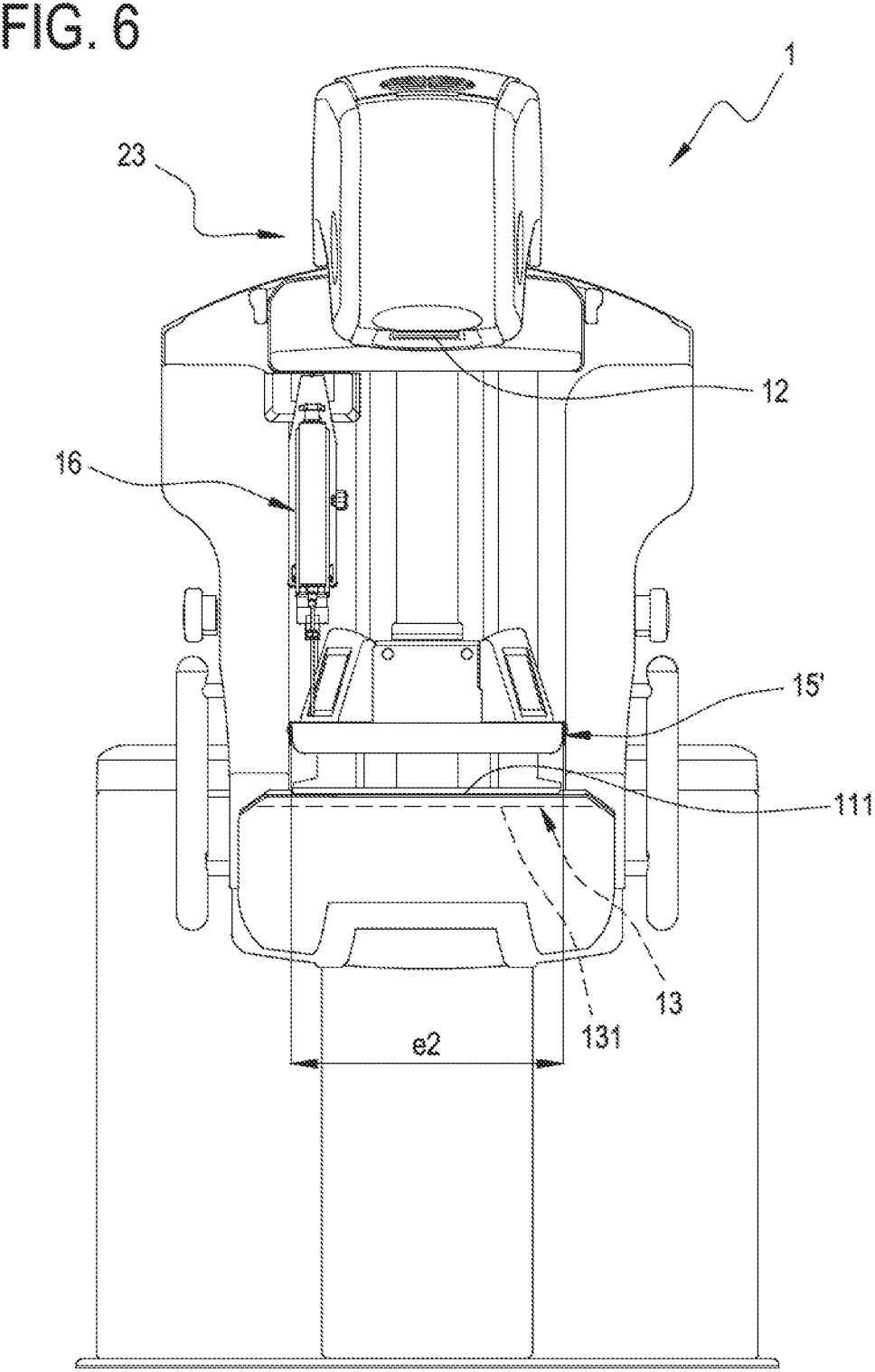
FIGS. 6 and 7 show front views of the apparatus of FIGS. 1-2, whilst a biopsy probe of the apparatus adopts, respectively, two different positions.
Figure 7:
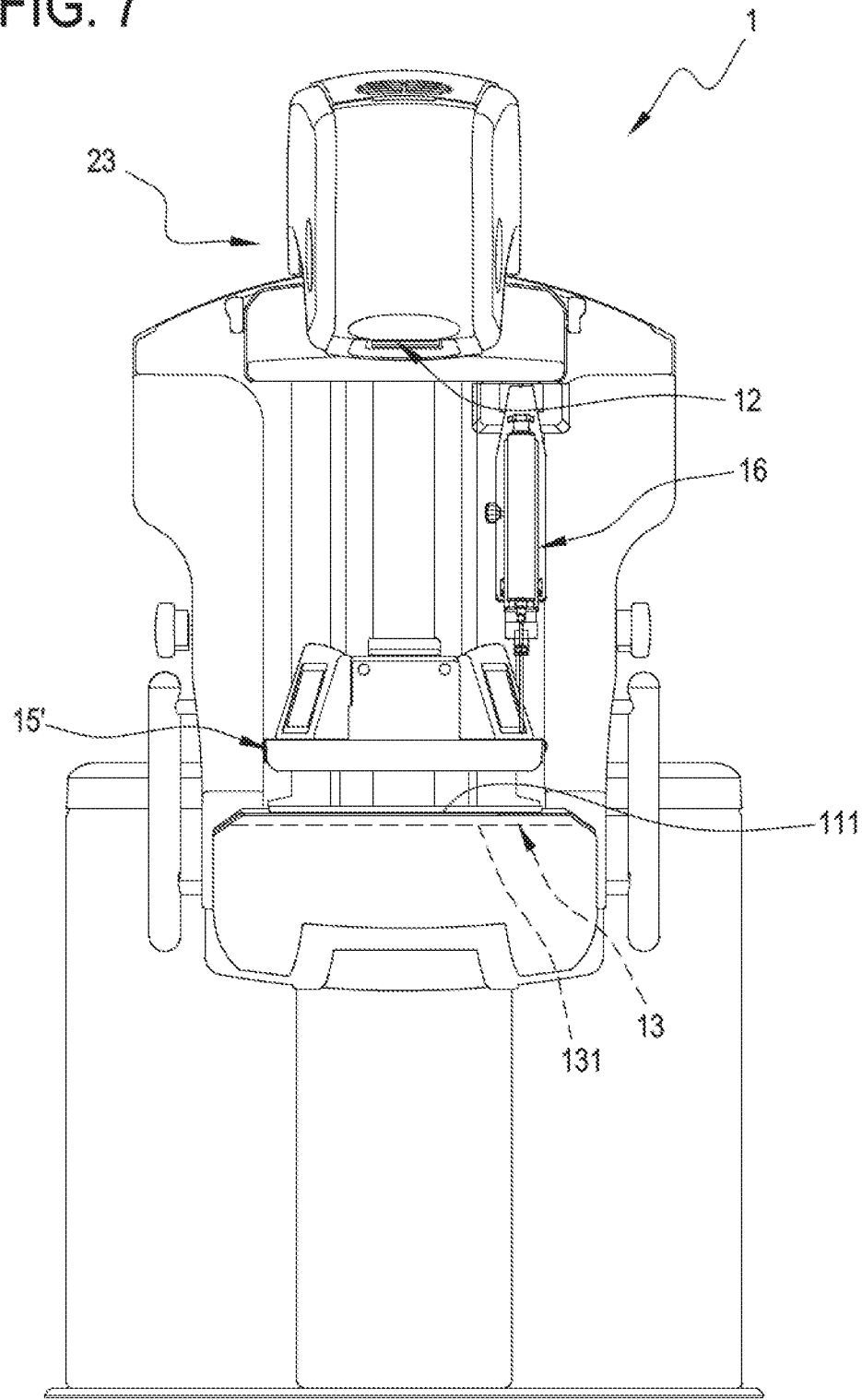

In FIGS. 3 to 5, the stabilizing element 15 belongs to a first type and is labelled 15. In FIGS. 6 and 7 the stabilizing element is labelled 15' since it belongs to a second type.

One or more of the features described with reference to the stabilizing 15 may be considered present in and/or also applicable to the stabilizing element 15', unless stated otherwise.

The apparatus 1 is configured so that the stabilizing element 15 can be subjected to a movement through the field and/or relative to the detection surface 131. This movement of the stabilizing element 15 is used to ensure that the stabilizing 15, as a function of the shape and/or the size and/or the positioning of the part of the body on the supporting surface 141, can stabilize optimally the part of the body on the supporting surface 141, in order to take the samples from the part of the body.

A position of the stabilizing element 15 relative to the detection surface 131 may be considered, which is to be considered as a position of the stabilizing element 15 relative to the above-mentioned reference system integral with the detection surface 131.

This movement of the stabilizing element 15 is designed to cause a variation of the position of the stabilizing element 15.

This movement of the stabilizing element 15 could comprise at least one translational component. An example of this translational component denotes by means of the double arrows T1 in FIG. 3. The translational component could be along the above-mentioned first axis Z.

The position of the stabilizing element 15 comprises at least the height at which a reference point of the stabilizing element 15 is positioned along and/or relative to the first axis Z. The reference point of the stabilizing element 15 is labelled o1 in FIG. 4. The height may be defined as the height of the stabilizing element 15 along the first axis Z.

This translational component of the movement of the stabilizing element 15 causes the variation of the height of the stabilizing element 15.

The stabilizing element 15' or 15 is shown, respectively, in FIGS. 8 and 9 in a schematic fashion.

In order to cause the movement of the stabilizing element 15, the apparatus 1 comprises a movement system of the stabilizing element 15. The movement system of the stabilizing element 15 is labelled 21 in FIGS. 1 and 2.

This movement of the stabilizing element 15 might comprise also or alternatively a translational component along the second axis Y lying on the detection surface 131 and/or a translational component along an axis at right angles to the first axis Z and the second axis Y.

The apparatus 1 comprises an automatic selection system 17.

The automatic selection system 17 comprises a processing unit 171.

The apparatus is configured so that the selection system 17 can automatically obtain or automatically know at least one of the following parameters: the current position of the stabilizing element 15 relative to the detection surface 131, current position of the probe 16 relative to the detection surface 131, dimensions of the stabilizing element 15, dimensions of the probe 16.

The overall size of the stabilizing element 15 may be considered as given by the shape and/or by the dimensions of the stabilizing element 15.

The overall size of the probe 16 may be considered as given by the shape and/or by the dimensions of the probe 16.

The overall size of the stabilizing element 15 may be considered as defined at least by the extension of the stabilizing element 15 along the above-mentioned first axis Z.

The extension of the stabilizing element 15 is labelled e1 in FIG. 4. It should be noted that the stabilizing element 15, in FIGS. 3-5, belongs to the first part, and is therefore labelled 15. The stabilizing element 15 is schematically illustrated in FIG. 9.

The extension of the stabilizing element 15' is labelled e2 in FIG. 6. It should be noted that the stabilizing element, in FIGS. 6-7, belongs to the second type, and is therefore labelled 15'. The stabilizing element 15' is schematically illustrated in FIG. 8.

The current position of the stabilizing element 15 relative to the detection surface 131 means the position which the stabilizing element 15 is adopting, relative to the reference system integral with the detection surface 131, when the selection system 17 obtains this position of the stabilizing element 15.

The current position of the probe 16 relative to the detection surface 131 means the position which the probe 16 is adopting, relative to the reference system integral with the detection surface 131, when the selection system 17 obtains this position of the probe 16.

The current position of the stabilizing element 15 relative to the detection surface 131 may be considered as comprising at least the current height of the stabilizing element 15 along the first axis Z and relative to the reference system integral with the detection surface 131.

In each of FIGS. 3-5 the current height of the stabilizing element 15 is different. In FIGS. 6 and 7 the current height of the stabilizing element 15' is equal.

The obtaining by the selection system 17 of the current position of the stabilizing element 15 may be considered as comprising at least one obtaining by the selection system 17 of the current value of the height of the stabilizing element 15.

The current position of the probe 16 relative to the detection surface 131 may be considered as comprising at least the current height of the probe 16 along the first axis Z and relative to the reference system integral with the detection surface 131. The current position of the probe 16 relative to the detection surface 131 may be considered as comprising at least one current orientation of the probe 16 about the axis of rotation W and relative to the reference system integral with the detection surface 131.

The current height of the probe 16 in FIGS. 3-5 is equal. In FIG. 6 the current height of the probe 16 is different from that of FIG. 7. In FIGS. 3-5 the current height of the probe 16 is different relative to both FIG. 6 and FIG. 7.

The current orientation of the probe 16 is the same in all the Figures from 3 to 7.

The obtaining by the selection system 17 of the current position of the probe 16 may be considered as comprising at least one obtaining by the selection system 17 of the current value of the height of the probe 16.

The obtaining by the selection system 17 of the current position of the probe 16 may be considered as comprising at least one obtaining by the selection system 17 of the current value of the orientation of the probe 16.

The obtaining by the selection system 17 of the overall size of the stabilizing element 15 may be considered as comprising at least one obtaining by the selection system 17 of the value of the extension of the stabilizing element 15.

The selection system 17 may comprise one or more sensors for detecting the at least one parameter, in order that the selection system 17 can obtain or know the at least one parameter.

The selection system 17 could comprise a first sensor 18, indicated in FIG. 3, for detecting the above-mentioned current height of the stabilizing element 15. The selection system 17 is configured so that the first sensor 18 can send to the processing unit 171 at least one signal S1 representing the current height of the stabilizing element 15.

The selection system 17 comprises a second sensor 19, shown in FIG. 3, for detecting the above-mentioned current height of the probe 16. The selection system 17 is configured so that the second sensor 19 can send to the processing unit 171 at least a signal S2 representing the current height of the probe 16.

In the example illustrated in the accompanying drawings, the selection system 17 comprises a third sensor 20, indicated in FIG. 3, for detecting the above-mentioned current orientation of the probe 16. The selection system 17 is configured so that the third sensor 20 can send to the processing unit 171 at least a signal S3 representing the current orientation of the probe 16.

The apparatus 1 may comprise an identification system by mean of which the selection system 17 can know the type to which the stabilizing element 15 belongs. From this type the selection system 17 can in turn know the above-mentioned dimensions of the stabilizing element 15. In particular, from the type the selection system 17 can know the above-mentioned extension of the stabilizing element 15.

The identification system may comprise an identifier mounted on the stabilizing element 15 and a reader of the identifier. The identifier may be, for example, of the RFID type, and the reader may be, for example, able to read the type of the stabilizing element 15 interacting with the identifier.

The selection system 17 is configured to perform automatically, as a function of the at least one parameter, a selection of one of the operating conditions of the field.

The operating condition selected is associated with a selected surface portion of the supporting surface 111. The selected surface portion is to be considered as the surface portion of the supporting surface 111 on which the field strikes when it adopts the selected operating condition.

The selected surface portion is to be understood in the sense that, when the field adopts the selected operating condition, to perform an acquiring of at least one X-ray image of the samples by means of the field and whilst the samples are positioned on the supporting surface 111, it is necessary to position these samples on the selected surface portion of the supporting surface 111, in such a way that are in the field.

The selection system 17 is configured for performing the selection in such a way as to limit, when the field adopts the selected operating condition and the samples are positioned inside the field and on the supporting surface 111 (and in particular on the above-mentioned selected surface portion of the supporting surface 111), the influence of the at least one parameter on the accuracy of the acquiring, by means of the generating system 12 and the detection system 13, of at least one X-ray image of the samples.

The selection system 17 is configured to calculate and/or derive, as a function of the at least one parameter and for each of the respective operating conditions of the field of X-rays, the possible influence of the at least one parameter on the accuracy. The selection system 17 is configured to derive and/or to calculate, as a function of the at least one parameter, the interference of the at least one parameter with the field of X-rays, for each of the operating conditions which the field may adopt. In this way the selection system 17 can select the operating condition so that, when the field adopts the selected operating condition and the samples are positioned in this field and on the supporting surface 111 (and in particular on the above-mentioned selected surface portion of the supporting surface 111), the influence of the at least one parameter on the accuracy of acquiring at least one X-ray image of the samples is minimal or in any case limited.

The accuracy of the acquiring of at least one X-ray image of the samples means the degree of precision and/or accuracy with which the at least one image allows the physical characteristics of the samples to be analyzed. An unwanted interference of the probe 16 or of the stabilizing element 15 with the field of X-rays, when the acquiring of the at least one X-ray image of the samples is performed, may worsen the degree of precision and/or accuracy with which the at least one image allows the physical characteristics of the samples to be analyzed.

The fact that the field of X-rays, when the acquiring of the X-ray image of the samples is performed, passes through the stabilizing element 15, is not necessarily and an unwanted interference. It should be noted, in effect, that is especially the edge zones of the stabilizing element 15, which respectively define the mutually opposite ends of the stabilizing element 15 along the first axis Z, that can, if they interfere with the field, significantly reduce the degree of accuracy and/or precision.

The selection system 17 is configured to generate a signal designed to signal to a user the selected operating condition. This signal comprises the highlighting on the above-mentioned selected surface portion.

The highlighting may comprise a signal, for example luminous, coming or generated from the selected surface portion.

The highlighting may comprise, for example, a luminous signal.

The highlighting may correspond, for example, to patterns or labels painted on the support 11.

Figure 10:
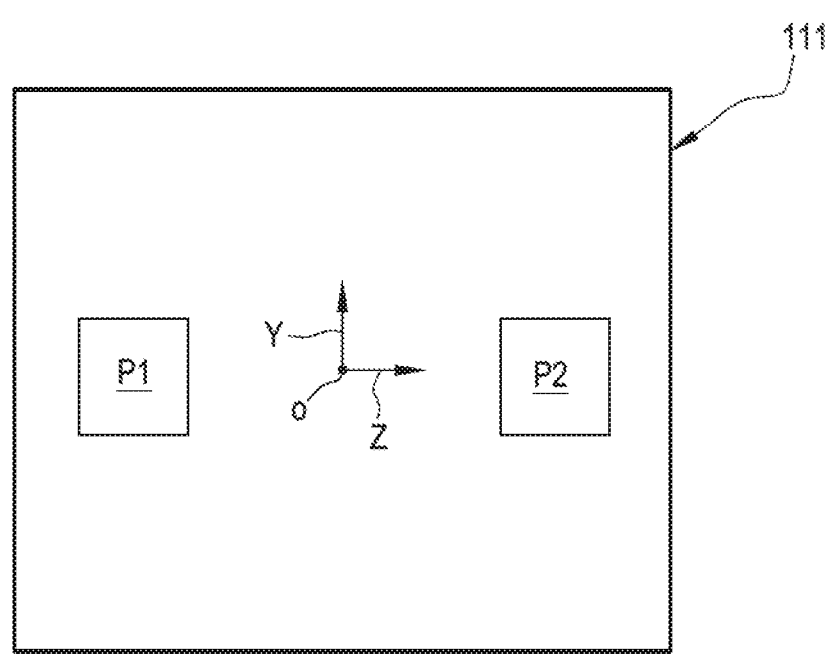
FIG. 10 is a plan view of a supporting surface of the apparatus of FIGS. 1 and 2, in order to show on the supporting surface the surface portions on which the field strikes when it adopts the first operating condition and second operating condition, respectively.

If the selected operating condition is the first operating condition of FIG. 8, labelled C1, then the selected surface portion would be the first portion labelled P1. A profile of the first portion P1 is shown in FIG. 8 and a plan view is shown in FIG. 10.

If the selected operating condition is the second operating condition of FIG. 8, labelled C2, then the selected surface portion would be the second portion labelled P2. A profile of the second portion P2 is shown in FIG. 8 and a plan view is shown in FIG. 10.

If the selected operating condition is the third operating condition of FIG. 9, labelled C3, then the selected surface portion would be the third portion labelled P3. A profile of the third portion P3 is shown in FIG. 9, and it is not shown, for reasons of clarity, in FIG. 10, as it would be superposed on the first portion P1.

The apparatus 1 may be configured so that the selection system 17 can automatically control the generating system 12 so that the field adopts the selected operating condition. The apparatus 1 may be configured so that the selection system 17 can send to the generating system 12 at least one control signal for adjusting the position of the source and the collimator in such a way that, when the source emits the X-rays, the field of X-rays adopts the selected operating condition. The control signal can be, for example, that labelled "k" in FIG. 3.

The selection system 17 could be configured so that the selection system 17 can obtain the above-mentioned overall size of the stabilizing element 15 and the above-mentioned current position of the stabilizing element 15.

The selection system 17 could be configured so that the fact that the above-mentioned selection is performed as a function of at least the current position of the stabilizing element 15 or is not performed as a function of the current position of the stabilizing element, depends on the dimensions of the stabilizing element 15.

The selection system 17 could be configured so that the selection system 17 can obtain the above-mentioned current position of the probe 16.

The selection system 17 could be configured so that the selection, if it is not performed as a function of the current position of the stabilizing element 15, is performed at least as a function of the current position of the probe 16.

The apparatus 1 could also be configured so that, even if the selection is performed as a function at least of the current position of the stabilizing element 15, the selection is performed in any case also as a function at least of the current position of the probe 16.

The selection system 17 could be configured so that the fact that the above-mentioned selection is performed as a function of at least the current orientation of the probe 16 or is not performed as a function of the current orientation of the probe 16, depends on the current height of the probe 16.

In a possible example embodiment of the apparatus 1, the selection system 17 is configured so that:
- if the above-mentioned extension of the stabilizing element 15 is less than or equal to a predetermined value, the selection is performed as a function at least of the current height of the stabilizing element 15;
- if the above-mentioned extension of the stabilizing element 15 is greater than this predetermined value, the selection is not performed as a function of the current height of the stabilizing element 15.

In this possible example embodiment of the apparatus 1, the selection system 17 is configured so that, both in the case wherein the selection is performed as a function of at least of the current height of the stabilizing element 15 and wherein the selection is not performed as a function of the current height of the stabilizing element 15, the selection can be performed as a function at least of the above-mentioned current height of the probe 16.

In this possible example embodiment of the apparatus 1, the selection system 17 is configured so that, if the current height of the probe 16 lies in a predetermined range of values, the selection is performed not as a function also of at least of the current orientation of the probe 16, and, if the current height of the probe 16 does not fall in this predetermined range of values, the selection is performed as a function also of at least of the current orientation of the probe 14.

The selection system 17 is configured to perform a logic process in order to perform the selection. The selection system 17 is configured so that the selection is performed by the processing unit 171. The processing unit 171 is programmed and/or configured to perform this logic process.

Figure 11:
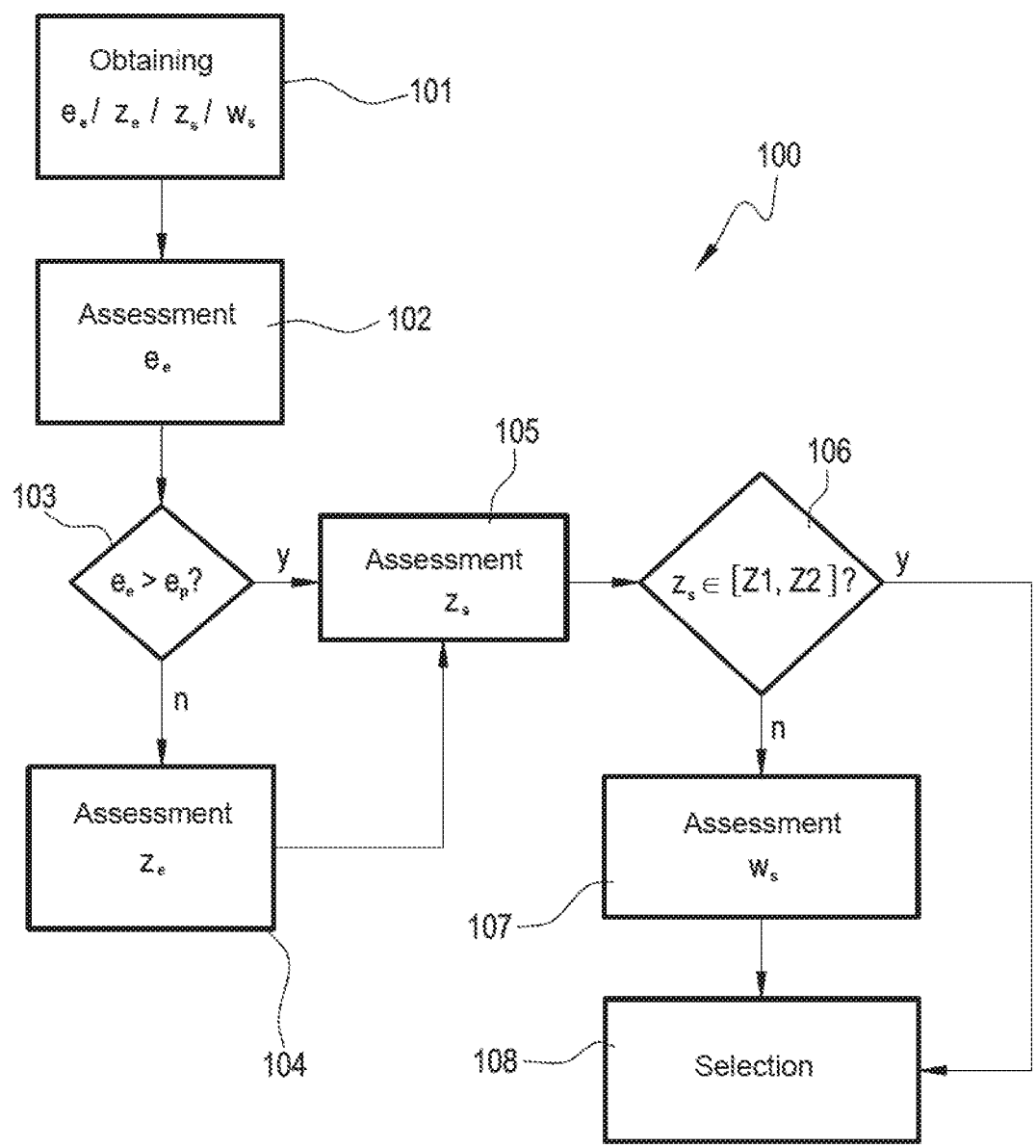
FIG. 11 is a flow diagram relative to a possible process for selecting an operating condition of the field, which may be performed automatically by the apparatus of FIGS. 1 and 2.

This process logic may be performed, for example, according to the flow diagram of FIG. 11. The processing unit 171 is configured and/or programmed for performing this logic process following a path defined by the arrows between the blocks of the flow diagram of FIG. 11.

FIG. 11 shows an obtaining block 101.

FIG. 11 shows a first assessment block 102, a second assessment block 104, a third assessment block 105, and a fourth assessment block 107.

FIG. 11 shows a first condition block 103 and a second condition block 106.

The obtaining block 101 indicates a step during which the processing unit 171 obtains the above-mentioned current value of the extension of the stabilizing element 15, the current value of the height of the stabilizing element 15, the current value of the height of the probe 16, the current value of the orientation of the probe 16. In the obtaining block 101, the current value of the extension of the stabilizing element is labelled ee, the current value of the height of the stabilizing element 15 is labelled ze, the current value of the height of the probe 16 is labelled zs, and the current value of the orientation of the probe 16 is labelled ws.

The first assessment block 102 indicates a step during which the processing unit 171 assesses the value obtained of the extension of the stabilizing element 15.

The first condition block 103 indicates a step during which the processing unit 171 determines whether the value obtained of the extension ee of the stabilizing element 15 is less than or equal to the predetermined value. The predetermined value, in the first condition block 103, is labelled "ep".

The second assessment block 104 indicates a step during which the processing unit 171 assesses the value obtained of the height ze of the stabilizing element 15.

The third assessment block 105 indicates a step during which the processing unit 171 assesses the value obtained of the height zs of the probe 16.

The second condition block 106 indicates a step during which the processing unit 171 determines whether the value obtained of the height zs of the probe 16 lies in a range of predetermined values. The predetermined range of values, in the second condition block 106, is represented as [Z1, Z2].

The fourth assessment block 107 indicates a step during which the processing unit 171 assesses the value obtained of the orientation ws of the probe 16.

There is a selection block 108 in the flow diagram 100 of FIG. 11. The selection block 108 indicates the step during which the processing unit selects an operating condition of the field of X-rays, for acquiring at least one X-ray image of the above-mentioned samples. The operating condition is selected in order to reduce as much as possible an unwanted interference of the stabilizing element 15 and/or of the probe 16 on the acquiring.

The flow diagram 100 of FIG. 11 is to be understood in the sense that if the path followed by the processing unit 171 for performing this logic process passes through the second assessment block 104, then the selecting step 108 occurs as a function at least of the value obtained of the height ze of the stabilizing element 15.

The flow diagram 100 of FIG. 11 is to be understood in the sense that if the path followed by the processing unit 171 for performing this logic process passes through the third assessment block 105, then the selecting step 108 occurs as a function at least of the value obtained of the height zs of the probe 16.

The flow diagram 100 of FIG. 11 is to be understood in the sense that if the path followed by the processing unit 171 for performing this logic process passes through the fourth assessment block 107, then the selecting step 108 occurs as a function at least of the value obtained of the orientation ws of the probe 16.

If the value obtained of the extension ee of the stabilizing element 15 is greater than the predetermined value ep, then the processing unit 171 will arrive at the block for execution of the selection 108, without passing the second assessment block 104. In this way the selection is not a function of the value obtained of the height ze of the stabilizing element 15.

If the value obtained of the extension ee of the stabilizing element 15 is less than or equal to the predetermined value ep, then the processing unit 171 will arrive at the block for execution of the selection 108, passing the second assessment block 104. In this way the selection is a function at least of the value obtained of the height ze of the stabilizing element 15.

In FIG. 9 the stabilizing element 15 is that of FIGS. 3-5, and the extension of the stabilizing element 15 is labelled e1 as in FIG. 4. In FIG. 8 stabilizing element 15' is that of FIGS. 6 and 7, and the extension of the stabilizing element 15' is labelled e2 as in FIG. 6.

For example, the extension of the stabilizing element 15', labelled e2 in FIGS. 6 and 8, may be considered greater than the predetermined value ep. For example, the extension of the stabilizing element 15, labelled e1 in FIGS. 4 and 9, may be considered less than the predetermined value ep.

In the case of FIG. 8, the selection system 17 performs the selection not as a function of the obtained value of the height ze of the stabilizing element 15', since the extension ee of the stabilizing element 15' is greater than the predetermined value ep. In the case of FIG. 9, the selection system 17 performs the selection at least as a function of the obtained value of the height ze of the stabilizing element 15', since the extension ee of the stabilizing element 15' is less than the predetermined value ep.

In that sense, in the flow diagram of FIG. 11, both if the value obtained of the extension ee of the stabilizing element 15 is greater than the predetermined value ep, and if the value obtained of the extension ee of the stabilizing element 15 is less than or equal to the predetermined value ep, the processing unit 171 passes in any case the third assessment block 105.

According to a logic process different than that of FIG. 11, the processing unit 171 could pass directly from the second assessment block 104 to the selection block 108. In the latter case the selection would be performed not as a function of the value obtained of the height zs of the probe 16 and not as a function of the value obtained of the orientation ws of the probe 16.

If the value obtained of the height zs of the probe 16 lies in the predetermined range [Z1, Z2], then the path followed by the processing unit 171 will arrive at the selection block 108 without passing the fourth assessment block 107. In this way the selection is not a function of the value obtained of the orientation ws of the probe 14.

If the value obtained of the height zs of the probe 16 does not lie in the predetermined range [Z1, Z2], then the path followed by the processing unit 171 will arrive at the selection block 108 passing the fourth assessment block 107. In this way the selection is also a function of at least the value obtained of the orientation ws of the probe 14.

The apparatus 1 may comprise at least one container for containing the samples.

The apparatus 1 may comprise a locking system configured to define a condition for locking the container on any surface portion of a group of predetermined surface portions of the supporting surface 111.

The group of surface portions may comprise, for example, the surface portions labelled P1 and P2 in FIGS. 8 and 10.

The locking system is configured so that, when the container adopts the locking condition, the container keeps the samples operatively positioned on the any surface portion of the group of surface portions.

In this way, the apparatus 1 can be used even if the supporting surface 111 is parallel or in any case not at right angles to the force of gravity, and therefore whilst the patient, from whom the samples have been taken, it is in the prone position.

The selection system 17 is configured so that the selection is performed so that the selected surface portion belongs to the above-mentioned group of predetermined surface portions.

It should be noted that the selection system 17 could also be configured for reaching the conclusion that the analysis of samples, on the basis of one or more of the above-mentioned parameters, is impossible.

It should be noted that the selection system 17 could be configured to perform the selecting as a function at least the dimensions of the probe, as well as its position and/or orientation.

It should be noted that the selection system 17 could be configured so that the above-mentioned selection is performed solely as a function of one of the above-mentioned conditions because the other conditions are not significant for the accuracy of the acquiring. For example, the system could be formed in such a way that the position of the probe never interferes with the field of X-rays defined by the operating conditions corresponding to the above-mentioned predetermined surface portions. The checking of this condition is implicit in the selection system 18 and is always performed during the definition of the method even if not actively considered by the processing unit 171. The apparatus 1 could also be configured to perform a mammography and a stereotaxic biopsy.

According to a second aspect, the invention relates to a method for analysing samples taken from the part of the body of a person. The samples can be considered to be taken by biopsy.

The method comprises a step of preparing the support 111, the generating system 12, the detector 13, the support 14 and the probe 16.

The method comprises a step of automatically obtaining the above-mentioned at least one of the parameters.

The method comprises an automatic selecting step during which the above-mentioned selection of one of the operating conditions of the field is performed.

In addition, the method might comprise a step of acquiring at least one X-ray image of the above-mentioned samples whilst the samples are positioned on the above-mentioned selected surface portion.

The step of acquiring X-ray images comprises the following steps:
generating the field of X-rays by means of the generating system 12;
obtaining, by the detector 131, at least one X-ray image of the field of X-rays passed through by the above-mentioned samples.

Each X-ray image of the field of X-rays passed through by the above-mentioned samples means the above-mentioned "X-ray image of the above-mentioned samples".

During the above-mentioned acquiring step, the samples can be kept in position on the above-mentioned selected surface position by means of the above-mentioned container. During the above-mentioned acquiring step the container may be in the above-mentioned locking condition in such a way as to stabilize the positioning of the samples on the positioned surface portion (even in cases in which the supporting surface 111 is not at right angles to the force of gravity, and even parallel to the force).

What is claimed is:

1. An apparatus for analysis of samples obtained from a part of a body of a person, comprising:
a samples support defining a samples supporting surface configured for positioning the samples on the samples supporting surface;
a generating system for generating an X-ray field configured to generate a field of X-rays, the generating system being configured to allow the field to adopt a plurality of different operating conditions;
an X-ray detector defining a detection surface and configured to detect an image of X-rays striking the detection surface, the apparatus being configured so that, when the field adopts any of the operating conditions, the X-rays of the field strike the detection surface after striking the samples supporting surface, in such a way that, when the field adopts any of the operating conditions and the samples are positioned inside the field and on the samples supporting surface, the apparatus acquires, by the generating system and the detection system, at least one X-ray image of the samples;

a body support which defines a body supporting surface for resting the part of the body on the body supporting surface;

a stabilizing element which extends along an extension surface for stabilizing the stabilizing element, the apparatus being configured to allow the stabilizing element to stabilize the positioning of the part of the body on the body supporting surface in order to perform a sampling of the samples;

a biopsy probe to perform the sampling;

an automatic selection system;

the generating system being configured so that the operating conditions differ from each other for orientation and/or positioning of the field of X-rays with respect to the detection surface and/or for at least a value of a dimension of the field of X-rays;

the selection system being configured to automatically obtain at least one parameter chosen from the following parameters: a current position of the stabilizing element relative to the detection surface, a current position of the probe relative to the detection surface, dimensions of the stabilizing element, and dimensions of the probe;

the selection system being configured to automatically perform, according to the at least one parameter, a selection of one of the operating conditions of the field, the operating condition selected being associated with a selected surface portion of the samples supporting surface, the selected surface portion being the surface portion striking the field when in the selected operating condition;

the selection system being configured to perform the selection in such a way as to limit, when the field adopts the selected operating condition and the samples are positioned inside the field and on the samples supporting surface, an influence of the at least one parameter on an accuracy of the acquisition, by the generating system and the detection system, of the at least one X-ray image of the samples;

wherein the apparatus is configured to allow the selection system to obtain the dimensions of the stabilizing element and the current position of the stabilizing element;

wherein the selection system is configured to perform, or not perform, the selection as a function of at least the current position of the stabilizing element, depending on the dimensions of the stabilizing element;

an identification system by which the selection system identifies a configuration of the stabilizing element, and thereby obtains the dimensions of the stabilizing element.

2. The apparatus according to claim 1, wherein the selection system is configured to generate a signal configured to signal to a user the selected operating condition, by highlighting the selected surface portion.

3. The apparatus according to claim 1, wherein the selection system is configured to control the generating system so that the field adopts the selected operating condition.

4. The apparatus according to claim 1, wherein the samples supporting surface coincides with the body supporting surface.

5. The apparatus according to claim 1, wherein the apparatus is configured so that the stabilizing element is subjected to a movement relative to the detection surface.

6. The apparatus according to claim 1,
wherein the apparatus is configured so that the selection system obtains the current position of the probe;
wherein the apparatus is configured so that the probe is subjected to a movement relative to the detection surface;
wherein the selection system is configured so that the selection, if not performed as a function of the position of the stabilizing element, is performed at least as a function of the current position of the probe.

7. The apparatus according to claim 6, wherein the current position of the probe comprises a current height of the probe along a first axis integral with the detection surface and a current orientation of the probe about an axis of rotation integral with the movement of the probe,
wherein the selection system is configured to perform, or not perform, the selection as a function of at least the current orientation of the probe, depending on the current height of the probe.

8. The apparatus according to claim 1, comprising:
a container for containing the samples;
a locking system configured to define a locking condition for locking the container on any surface portion of a group of surface portions of the samples supporting surface;
the locking system being configured so that, when the container adopts the locking condition, the container keeps the samples operatively positioned on the any surface portion of the group of surface portions,
wherein the selection system is configured so that the selected surface portion belongs to the group of surface portions.

9. A method for the analysis of samples picked up from a part of a body of a person, comprising:
preparing a samples support defining a samples supporting surface for the positioning on the samples supporting surface of the samples;
preparing a system for generating an X-ray field configured to generate a field of X-rays, the generating system being configured to allow field to adopt a plurality of different operating conditions;
preparing an X-ray detector defining a detection surface and configured to detect the image of X-rays striking the detection surface;
preparing a body support which defines a body supporting surface for resting the part of the body on the body supporting surface;
preparing a stabilizing element which extends along a surface of extension of the stabilizing element;
preparing a biopsy probe to perform the sampling;
the preparing the stabilizing element being performed in such a way that the stabilizing element stabilizes the positioning of the part of the body on the body supporting surface in order to perform a sampling of the samples;
the preparing the generating system and the detection system being performed in such a way that, when the field adopts any of the operating conditions, the X-rays of the field strike the detection surface after striking the samples supporting surface;
the preparing the generating system and the detection system being performed in such a way that, when the field adopts any of the operating conditions and the samples are positioned inside the field and on the samples supporting surface, the generating system and the detection system perform an acquisition of at least one X-ray image of the samples;
automatically obtaining at least one parameter chosen from the following parameters: the current position adopted by the stabilizing element relative to the detection surface, current position adopted by the probe relative to the detection surface, dimensions of the stabilizing element, dimensions of the probe;

automatically selecting one of the operating conditions of the field, the operating condition selected being associated with a selected surface portion of the samples supporting surface, the selected surface portion being the surface portion on which it strikes the field when it adopts the selected operating condition;

the selecting being performed as a function at least of the parameter;

the selecting being performed in such a way as to limit, when the field adopts the selected operating condition and the samples are positioned inside the field and on the samples supporting surface, an influence of the at least one parameter on the accuracy of the acquisition, by means of the generating system and the detection system, of at least one X-ray image of the samples;

obtaining the dimensions of the stabilizing element and the current position of the stabilizing element;

performing, or not performing, the selecting as a function of at least the current position of the stabilizing element, depending on the dimensions of the stabilizing element;

identifying a configuration of the stabilizing element, and thereby obtaining the dimensions of the stabilizing element.

10. An apparatus for analysis of samples obtained from a part of a body of a person, comprising:

a samples support defining a samples supporting surface configured for positioning the samples on the samples supporting surface;

a generating system for generating an X-ray field configured to generate a field of X-rays, the generating system being configured to allow the field to adopt a plurality of different operating conditions;

an X-ray detector defining a detection surface and configured to detect an image of X-rays striking the detection surface, the apparatus being configured so that, when the field adopts any of the operating conditions, the X-rays of the field strike the detection surface after striking the samples supporting surface, in such a way that, when the field adopts any of the operating conditions and the samples are positioned inside the field and on the samples supporting surface, the apparatus acquires, by the generating system and the detection system, at least one X-ray image of the samples;

a body support which defines a body supporting surface for resting the part of the body on the body supporting surface;

a stabilizing element which extends along an extension surface for stabilizing the stabilizing element, the apparatus being configured to allow the stabilizing element to stabilize the positioning of the part of the body on the body supporting surface in order to perform a sampling of the samples;

a biopsy probe to perform the sampling;

an automatic selection system;

the generating system being configured so that the operating conditions differ from each other for orientation and/or positioning of the field of X-rays with respect to the detection surface and/or for at least a value of a dimension of the field of X-rays;

the selection system being configured to automatically obtain at least one parameter chosen from the following parameters: a current position of the stabilizing element relative to the detection surface, a current position of the probe relative to the detection surface, dimensions of the stabilizing element, and dimensions of the probe;

the selection system being configured to automatically perform, according to the at least one parameter, a selection of one of the operating conditions of the field, the operating condition selected being associated with a selected surface portion of the samples supporting surface, the selected surface portion being the surface portion striking the field when in the selected operating condition;

the selection system being configured to perform the selection in such a way as to limit, when the field adopts the selected operating condition and the samples are positioned inside the field and on the samples supporting surface, an influence of the at least one parameter on an accuracy of the acquisition, by the generating system and the detection system, of the at least one X-ray image of the samples;

wherein the apparatus is configured so that the selection system obtains the current position of the probe;

wherein the apparatus is configured so that the probe is subjected to a movement relative to the detection surface;

wherein the selection system is configured so that the selection, if not performed as a function of the position of the stabilizing element, is performed at least as a function of the current position of the probe;

wherein the current position of the probe comprises a current height of the probe along a first axis integral with the detection surface and a current orientation of the probe about an axis of rotation integral with the movement of the probe, wherein the selection system is configured to perform, or not perform, the selection as a function of at least the current orientation of the probe, depending on the current height of the probe.

11. The apparatus according to claim 10, wherein the selection system is configured to generate a signal configured to signal to a user the selected operating condition, by highlighting the selected surface portion.

12. The apparatus according to claim 10, wherein the selection system is configured to control the generating system so that the field adopts the selected operating condition.

13. The apparatus according to claim 10, wherein the samples supporting surface coincides with the body supporting surface.

14. An apparatus for analysis of samples obtained from a part of a body of a person, comprising:

a samples support defining a samples supporting surface configured for positioning the samples on the samples supporting surface;

a generating system for generating an X-ray field configured to generate a field of X-rays, the generating system being configured to allow the field to adopt a plurality of different operating conditions;

an X-ray detector defining a detection surface and configured to detect an image of X-rays striking the detection surface, the apparatus being configured so that, when the field adopts any of the operating conditions, the X-rays of the field strike the detection surface after striking the samples supporting surface, in such a way that, when the field adopts any of the operating conditions and the samples are positioned inside the field and on the samples supporting surface, the apparatus acquires, by the generating system and the detection system, at least one X-ray image of the samples;

a body support which defines a body supporting surface for resting the part of the body on the body supporting surface;

a stabilizing element which extends along an extension surface for stabilizing the stabilizing element, the apparatus being configured to allow the stabilizing element to stabilize the positioning of the part of the body on the body supporting surface in order to perform a sampling of the samples;

a biopsy probe to perform the sampling;

an automatic selection system;

the generating system being configured so that the operating conditions differ from each other for orientation and/or positioning of the field of X-rays with respect to the detection surface and/or for at least a value of a dimension of the field of X-rays;

the selection system being configured to automatically obtain at least one parameter chosen from the following parameters: a current position of the stabilizing element relative to the detection surface, a current position of the probe relative to the detection surface, dimensions of the stabilizing element, and dimensions of the probe;

the selection system being configured to automatically perform, according to the at least one parameter, a selection of one of the operating conditions of the field, the operating condition selected being associated with a selected surface portion of the samples supporting surface, the selected surface portion being the surface portion striking the field when in the selected operating condition;

the selection system being configured to perform the selection in such a way as to limit, when the field adopts the selected operating condition and the samples are positioned inside the field and on the samples supporting surface, an influence of the at least one parameter on an accuracy of the acquisition, by the generating system and the detection system, of the at least one X-ray image of the samples;

a container for containing the samples;

a locking system configured to define a locking condition for locking the container on any surface portion of a group of surface portions of the samples supporting surface;

the locking system being configured so that, when the container adopts the locking condition, the container keeps the samples operatively positioned on the any surface portion of the group of surface portions, wherein the selection system is configured so that the selected surface portion belongs to the group of surface portions.

15. The apparatus according to claim 14, wherein the selection system is configured to generate a signal configured to signal to a user the selected operating condition, by highlighting the selected surface portion.

16. The apparatus according to claim 14, wherein the selection system is configured to control the generating system so that the field adopts the selected operating condition.

17. The apparatus according to claim 14, wherein the samples supporting surface coincides with the body supporting surface.

* * * * *